United States Patent [19]

Engelson

[11] Patent Number: 5,722,424
[45] Date of Patent: Mar. 3, 1998

[54] MULTI-COATING STAINLESS STEEL GUIDEWIRE

[75] Inventor: Erik T. Engelson, Menlo Park, Calif.

[73] Assignee: Target Therapeutics, Inc., Fremont, Calif.

[21] Appl. No.: 535,806

[22] Filed: Sep. 29, 1995

[51] Int. Cl.⁶ ......................................................... A61B 5/00
[52] U.S. Cl. ............................... 128/772; 604/95; 128/657; 128/658
[58] Field of Search .......................... 128/772, 657–8; 604/95.6, 780–3; 428/380

[56] References Cited

U.S. PATENT DOCUMENTS

| | | |
|---|---|---|
| 4,682,607 | 7/1987 | Vaillancourt et al. . |
| 4,884,579 | 12/1989 | Engelson . |
| 5,067,491 | 11/1991 | Taylor, II et al. . |
| 5,095,915 | 3/1992 | Engelson . |
| 5,107,852 | 4/1992 | Davidson et al. .................. 128/772 |
| 5,129,890 | 7/1992 | Bates et al. . |
| 5,174,295 | 12/1992 | Christian et al. . |
| 5,213,111 | 5/1993 | Cook et al. . |
| 5,217,026 | 6/1993 | Stoy et al. . |
| 5,228,453 | 7/1993 | Sepetka . |
| 5,259,393 | 11/1993 | Corso, Jr. et al. . |
| 5,267,574 | 12/1993 | Viera et al. . |
| 5,303,714 | 4/1994 | Abele et al. . |
| 5,333,620 | 8/1994 | Moutafis et al. . |
| 5,346,508 | 9/1994 | Hastings . |
| 5,372,144 | 12/1994 | Mortier et al. . |
| 5,380,320 | 1/1995 | Morris . |
| 5,402,799 | 4/1995 | Colon et al. . |
| 5,404,887 | 4/1995 | Prather . |
| 5,409,015 | 4/1995 | Palermo . |
| 5,443,455 | 8/1995 | Hergenrother et al. ............... 428/380 |
| 5,452,726 | 9/1995 | Burmeister et al. .................. 128/772 |
| 5,465,733 | 11/1995 | Hinohara et al. ..................... 128/772 |

FOREIGN PATENT DOCUMENTS 4-9162  1/1992  Japan .

*Primary Examiner*—Robert A. Hafer
*Assistant Examiner*—Pamela L. Wingood
*Attorney, Agent, or Firm*—Morrison & Foerster

[57] ABSTRACT

This is a surgical instrument. It is a guidewire made of a stainless steel alloy core which is coated with a non-hydrophilic lubricious polymer on the majority of its length located proximally and a hydrophilic polymer located at the majority of the remaining distal length of the guidewire. Preferably, the guidewire has a polymeric tie layer located between the metallic core of the guidewire assembly and the hydrophilic polymeric layer. The metallic core is one of a number of stainless steels so to preserve its torque transmitting capabilities. Desirably the outside diameter of the guidewire is constant from the distal end to the proximal end. The metallic core may be tapered at appropriate locations along the guidewire assembly.

9 Claims, 1 Drawing Sheet

1

MULTI-COATING STAINLESS STEEL GUIDEWIRE

FIELD OF THE INVENTION

This invention is a surgical instrument. It specifically relates to a guidewire made of a stainless steel alloy core which is coated with a non-hydrophilic lubricious polymer on the majority of its length located proximally and a hydrophilic polymer located at the majority of the remaining distal length of the guidewire. Preferably, the guidewire has a polymeric tie layer located between the metallic core of the guidewire assembly and the hydrophilic polymeric layer. The metallic core is one of a number of stainless steels so to maintain its torque transmitting and bending stiffness capabilities. Desirably the outside diameter of the guidewire is constant from the distal end to the proximal end. The metallic core may be tapered at appropriate locations along the guidewire assembly.

BACKGROUND OF THE INVENTION

As costs of medical care increase, the need for more precise and less traumatic medical procedures has increased as well. These procedures result in fewer effects ancillary to those necessary for the specific treatment. Hospital stays may be lessened. Recovery times may be improved. Vascular catheters are used to treat a variety of maladies formerly treated by drastic surgery. For instance, current high performance catheters are used in the treatment of berry aneurysms in the brain, various vascular accidents (such as strokes and contusions), percutaneous transcatheter angioplasty (PTCA), and the like.

Although various different catheter designs may be used in attaining selected treatment sites, many catheters used for the delivery of therapeutic materials such as drugs and vasoocclusive devices are over-the-wire catheters. Other catheters used in the vascular system may be of a design which is flow-directed. A few flow-directed catheters are designed to use a simple distal end which is quite floppy and able to be carried along by the flow of blood through the body. Other flow-directed devices utilize small balloons at their distal end which act as "drag anchors" in pulling that distal end through the vascular path. Flow-directed catheters have the advantage of quickly approaching a site through the vasculature if the site is in a high blood flow region. If the selected site is not in the highest velocity courseway, there is little or no chance that the catheter will reach the desired site.

Over-the-wire catheters are especially useful in treating or diagnosing regions of the body which are difficult to reach because of their location, e.g., at the end of distal and complicated routes through the vasculature. This is so since, unlike catheters typically used in the region of the heart, vascular catheters for remote vasculature do not have sufficient strength, stiffness, and ability to transmit torque to allow movement of the catheter by itself to the selected remote site. Consequently, guidewires are used to provide column strength and torsional strength to the overall catheter/guidewire assembly so that these fine vascular catheters can be tracked over the guidewire and steered through pertinent vessels. See, for instance, the disclosure in U.S. Pat. No. 4,884,579 to Engelson.

In general, the method of using a guidewire with a highly flexible catheter is as follows: a torqueable guidewire having a distal, bent end is guided by alternately rotating and advancing the wire in the vascular pathway to the target site. The distal bend allows the attending physician the choice (with the aid of fluoroscopy) to select a route through bends and "Y's" in the vasculature to the target site. As the guidewire is moved along the selected route, the catheter is typically advanced along the guidewire in increments. It is critical that the catheter be able to track the guidewire along the route in which the guidewire has been placed. That is to say that the catheter must not be so stiff at its distal end (for a selected guidewire) that the catheter pulls the guidewire from its previously selected route. Additionally the guidewire must be flexible enough to be able to follow the chosen route. Furthermore, both the guidewire and the catheter must be of sufficient resilience that they not easily kink when a difficult or tight region of vasculature is encountered. The guidewire must ideally have the ability to transmit torque along its length in a controllable fashion—that is to say that a selected wire rotation at the wire's proximal end produces a corresponding rotation at the distal end—so to allow the physician to steer the guidewire as needed. The need to penetrate farther into the vasculature of extremely soft organs such as the brain and liver provide great demands on the physical description of and material selection for guidewires.

If the wire is too thin along its entire length, it is often difficult to transmit torque in a controlled manner along that wire length. Further, the wire may buckle with axial movement due to low column strength.

One solution to many of these problems has been through appropriate choice of material for the guidewire. One such choice of materials is of alloys containing nickel and titanium and which has been treated in a specific fashion to result in a class generally known as nitinols. Typical of such guidewires are those shown in Bates, U.S. Pat. No. 5,129,890 and to Cook, U.S. Pat. No. 5,213,111. Some improvements to such device is using nickel titanium alloys may be found in U.S. Pat. No. 5,409,015 to Palermo. These alloys are especially suitable for accessing deep into vasculature within soft tissue in that for properly chosen alloys, the guidewires have the ability to undergo major bending without any plastic deformation. Although nitinol guidewires are very suitable for deep access into the vasculature, an offset in performance is typically attained because the alloy itself is quite resilient and stores significant mechanical energy. Said another way: a nitinol guidewire that is flexible enough to enter deep tortuous pathways may be difficult to use: a.) the user may not be able controllably to twist or torque the tip of the guidewire into an appropriate position, and b.) the excessive flexibility doesn't permit tracking of the catheter since the stiffer catheter may pull the guidewire from its preselected route. This usability parameter is one which is typically attributable to the size and material found in the more proximal portions of the guidewire.

Increasing the size of the proximal portion of the guidewire raises the lateral stiffness of the guidewire. Increasing the diameter of a nitinol guidewire to a point where the torqueability is improved sometimes will result in a guidewire having a diameter which is too large for easy physical manipulation.

Another tack taken in improving manipulation and insertability of guidewires has been that of coating the wires with various lubricating materials. An early lubricating material has been high molecular weight silicon-derived oils or near-greases. Other more substantial (and permanent) coverings such as polytetrafluoroethylene (TEFLON) and various hydrophilic coatings have also been suggested as coatings for these guidewires. Lubricious coatings on guidewires provide a number of benefits. Proper selection of coatings lowers the resistance to axial movement of the guidewire within the catheter. Similarly, the coatings may be used to lower the resistance of the guidewire within the catheter as it is turned or torqued. Slippery coatings on the guidewire lessen the chance that the catheter will kink as it is moved axially along the guidewire.

U.S. Pat. No. 5,129,890 to Bates, et. al was mentioned in passing above. This patent describes a guidewire having a shaped-memory material. The guidewire's central core has an elongated coil attached distally. A thin polymer sleeve, preferably of polyurethane, is positioned adjacent the core wire. The polymer sleeve provides a base for a hydrophilic polymer coating which is placed on the outer periphery of the underlying polymer sleeve. An alternate embodiment of the guidewire is a one in which the proximal portion of the inner polymer sleeve is not coated with a hydrophilic covering.

Another variation is shown in U.S. Pat. No. 4,884,579 to Engelson. Engelson teaches a guidewire having a distal section which allows greater purchase with the vessel walls through which it is placed; that is to say the distal portion is a higher friction portion of the guidewire than is the portion just proximal of the higher friction section. The somewhat more proximal section is covered with a material which renders that section more lubricious. Suitable coating materials include TEFLON, polyurethane, or materials which form the support for hydrophilic polymers.

U.S. Pat. No. 5,213,111, to Cook, shows a composite guidewire made up of a thin stainless steel wire radially surrounded by a shape-memory alloy, such as a nickel-titanium alloy. The guidewire assembly is said to be coated with a polymer layer and 70%–80% of the distal-most portion of the wire can be coated with a hydrophilic polymer to increase lubricity.

U.S. Pat. No. 5,228,453 to Sepetka, shows a guidewire made up of a flexible, torqueable proximal wire section, a more flexible intermediate section with a flexible polymeric tube covering, and a most flexible distal end section. A helical ribbon coil is wrapped about the intermediate core segment between the wire core and the polymer tube covering to increase radio-opacity and to improve torque transmission while retaining flexibility.

U.S. Pat. No. 5,259,393 to Corso, Jr. et. al. describes a guidewire having controlled radio-capacity at the guidewire's distal tip. A single spring mounted on the guidewire has a tightly coiled region and a second more loosely coiled and less radio-opaque region. The loosely coiled region may be coated with a polymer to avoid roughness due to the presence of the coil.

U.S. Pat. No. 5,333,620 to Moutafis, et. al. describes a guidewire having a metal wire core and a high performance plastic sleeve extruded over that core. A high performance plastic is said to be one which has a flexural modulus of at least 150 ksi and an elongation (at yield) of at least two percent (2%). The preferred high performance plastic is a polysulfone. Other suitable high performance plastics are said to include polyimide, polyetheretherketone (PEEK), polyaryleneketone, polyphenylene sulfide, polyarylene sulfide, polyamideimide, polyetherimide, polyimidesulfone, polyarylsulfone, polyarylethersulfone, and certain polyesters. The coextruded compliant jacket is then said to be completely coated with lubricious material which preferably is hydrophilic. The preferred lubricious materials include complexes of polyurethane and polyvinylpyrrolidone.

U.S. Pat. No. 5,372,144 to Mortier, et. al. describes a guidewire having a sleeve element exterior to a guidewire core. The sleeve element apparently is a polymeric material of high elasticity and low flexural modulus such as polyurethane.

None of these documents show a high torque capability guidewire comprising stainless steel and a composite covering of sprayed polytetrafluoroethylene proximally and a hydrophilic covering distally.

SUMMARY OF THE INVENTION

This invention is a guidewire assembly of relatively constant diameter. It is comprised of a stainless steel core which may be tapered at various locations along the length of the wire assembly. Proximally, the core is coated with sprayed polytetrafluoroethylene or other high performance lubricious polymer. Distally (but adjunct the proximal polymeric covering) may either be a hydrophilic lubricious polymeric composition placed directly on the core wire or attached to the core wire via the use of a tie layer of some sort. Suitable tie layers include polyesters such as polyurethane and polyethyleneterephthalate (PET). A distally placed radiopaque coil may be attached to the distal-most portion of the guidewire.

This specific combination of coating and core wire materials results in a catheter which is highly maneuverable because of its distal response to proximal input and yet may be introduced into a soft organ such as the brain or liver nearly to the extent that a much more compliant nitinol guidewire could be.

DESCRIPTION OF THE INVENTION

As noted above, this invention is a stainless steel guidewire having a generally constant diameter and multiple coatings along its length.

Figure 1:
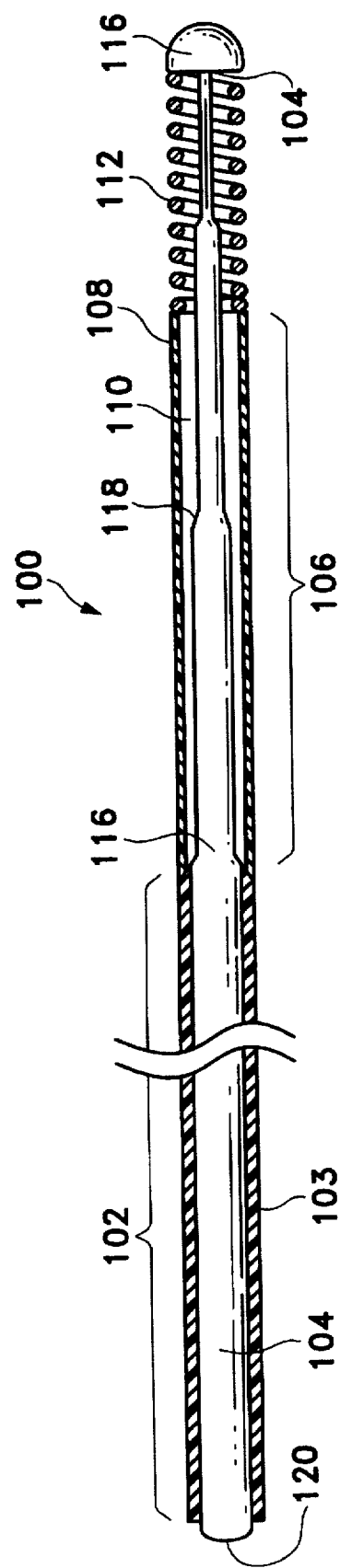
FIGS. 1 and 2 show side view, partial cutaway drawings of guidewires made according to this invention.

FIG. 1 shows one variation of the invention. FIG. 1 shows a guidewire (100) made according to the invention which has a more proximal region (102) having a permanent, spray-applied coating (103) of a fluorocarbon polymer, e.g., a polytetrafluoroethylene such as a Teflon, or other thin tough lubricious polymer such as polyarylenes or polysulfones applied directly onto the core wire (104) and a more-distal region (106) adjacent to the more-proximal region (102). The more-distal region (106) has a composite covering made up of an outer hydrophilic covering (108) and an inner tie layer (110). Finally, the most distal section of the guidewire (100) comprises a radio-opaque coil (112) which surrounds at least a portion of the core wire (104). The radio-opaque coil (112) lends a measure of directablity and shapeability to the guidewire assembly (100) in addition to providing an easily viewable terminus to the guidewire (100) when viewed with the aid of a fluoroscope. The radio-opaque coil (112) may be used with a ribbon (114) which variously may help with formation of the tip during the surgical procedure and with protection from the eventuality of the coil (112) separating from the tip.

The guidewire (100) typically has a total length typically between about 50 and 300 centimeters. The proximal section (102) preferably has a uniform outer diameter (along its length) of about 0.010 to 0.025 inches, preferably 0.010 to 0.018 inches. The relatively more flexible distal section (106) extends for 3 to 45 centimeters or more of the distal end of the guidewire (100). One or more of the more distal section (106) and the more proximal (102) section may contain portions which are progressively smaller in diameter than the more proximal sections. The junctions may be a step (typically not desired) or a taper such as is shown in the Figures at, e.g., at (116) and (118). Alternatively, the progression from larger diameter to smaller diameter in the core wire (104) may be via one or more long tapered sections. The fine wire coil (112) may be radiopague and made from materials including but not limited to platinum and its alloys.

Because this catheter is designed to have high torque transmission capabilities, the core wire (104) should have a diameter in its proximal section of between 9 and 18 mils generally between the proximal end (120) and the beginning of the first taper or joint (116). The material making up the core wire (104) may be 303, 304, 304V, or 316 stainless steel. The overall thickness of the coating (103) on this section (102) should be no greater than about 1.0 mil and preferably is between 0.1 mils and 0.5 mils. The coating (103) on the more proximal portion (102) is adjacent the coatings (108) and (110) on the more distal section (106). The material of the more proximal coating (103) is different than the materials in the coating layers (108) and (110). As noted above, the most desirable way on providing a polytetrafluoroethylene coating of minimal thickness on the inventive guidewire is by spray coating. Application of other protective polymers, such as the noted parylene coatings, may be by other methodology.

There are a variety of "parylene" polymers (e.g., polyxyxylene) based on para-xylylene. These polymers are typically placed onto a substrate by vapor phase polymerization of the monomer. Parylene N coatings are produced by vaporization of a di(P-xylylene) dimer, pyrollization, and condensation of the vapor to produce a polymer that is maintained at a comparatively lower temperature. In addition to parylene-N, parylene-C is derived from di(monochloro-P-xylylene) and parylene-D is derived from di(dichloro-P-xylylene). There are a variety of known ways to apply parylene to substrates. Their use in surgical devices has been shown, for instance, in U.S. Pat. No. 5,380,320 (to J. R. Morris), in U.S. Pat. No. 5,174,295 (to Christian et al.), in U.S. Pat. No. 5,067,491 (to Taylor et al.) and the like, the entirety of which are incorporated by reference.

This combination of more-proximal section material, core wire diameter, and coating material (along with its method of application) provides a guidewire which, when constructed with the combination of materials in the more proximal section as is discussed below, results in enhanced ease of use.

As shown in FIG. 1, the guidewire core (104) is covered in the more distal section (106) with hydrophilic polymers including those made from monomers such as ethylene oxide and its higher homologs; 2-vinyl pyridine; N-vinylpyrrolidone; polyethylene glycol acrylates such as mono-alkoxy polyethylene glycol mono(meth) acrylates, including mono-methoxy triethylene glycol mono (meth) acrylate, mono-methoxy tetraethylene glycol mono (meth) acrylate, polyethylene glycol mono (meth) acrylate; other hydrophilic acrylates such as 2-hydroxyethylmethacrylate, glycerylmethacrylate; acrylic acid and its salts; acrylamide and acrylonitrile; acrylamidomethylpropane sulfonic acid and its salts cellulose, cellulose derivatives such as methyl cellulose ethyl cellulose, carboxymethyl cellulose, cyanoethyl cellulose, cellulose acetate, polysaccharides such as amylose, pectin, amylopectin, alginic acid, and cross-linked heparin; maleic anhydride; aldehydes. These monomers may be formed into homopolymers or block or random copolymers. The use of oligomers of these monomers in coating the guidewire for further polymerization is also an alternative. Preferred precursors include ethylene oxide; 2-vinyl pyridine; N-vinylpyrrolidone and acrylic acid and its salts; acrylamide and acrylonitrile polymerized (with or without substantial crosslinking) into homopolymers, or into random or block copolymers.

Additionally, hydrophobic monomers may be included in the coating polymeric material in an amount up to about 30% by weight of the resulting copolymer so long as the hydrophilic nature of the resulting copolymer is not substantially compromised. Suitable monomers include ethylene, propylene, styrene, styrene derivatives, alkylmethacrylates, vinylchloride, vinylidenechloride, methacrylonitrile, and vinyl acetate. Preferred are ethylene, propylene, styrene, and styrene derivatives.

The polymeric coating may be cross-linked using various techniques, e.g., by light such as ultraviolet light, heat, or ionizing radiation, or by peroxides or azo compounds such as acetyl peroxide, cumyl peroxide, propionyl peroxide, benzoyl peroxide, or the like. A polyfunctional monomer such as divinylbenzene, ethylene glycol dimethacrylate, trimethylolpropane, pentaerythritol di- (or tri- or tetra-) methacrylate, diethylene glycol, or polyethylene glycol dimethacrylate, and similar multifunctional monomers capable of linking the monomers and polymers discussed above.

Polymers or oligomers applied using the procedure described below are activated or functionalized with photoactive or radiation-active groups to permit reaction of the polymers or oligomers with the underlying polymeric surface, the "tie layer", when such tie layer is used. In FIG. 1, the tie layer (110) is found beneath the hydrophilic layer (108). Suitable activation groups include benzophenone, thioxanthone, and the like; acetophenone and its derivatives specified as:

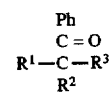

where $R^1$ is H, $R^2$ is OH, $R^3$ is Ph; or
$R^1$ is H, $R^2$ is an alkoxy group including —OCH$_3$, —OC$_2$H$_3$, $R^3$ is Ph; or
$R^1 = R^2 =$ an alkoxy group, $R^3$ is Ph; or
$R^1 = R^2 =$ an alkoxy group, $R^3$ is H; or
$R^1 = R^2 =$ Cl, $R^3$ is H or Cl.

Other known activators are suitable.

The polymeric hydrophilic coating (108) may then be linked with the substrate using known and appropriate techniques selected on the basis of the chosen activators, e.g., by ultraviolet light, heat, or ionizing radiation. Crosslinking with the listed polymers or oligomers may be accomplished by use of peroxides or azo compounds such as acetyl peroxide, cumyl peroxide, propionyl peroxide, benzoyl peroxide, or the like. A polyfunctional monomer such as divinylbenzene, ethylene glycol dimethacrylate, trimethylolpropane, pentaerythritol di- (or tri- or tetra-) methacrylate, diethylene glycol, or polyethylene glycol dimethacrylate, and similar multifunctional monomers capable of linking the polymers and oligomers discussed above is also appropriate for this invention.

The polymeric hydrophilic coating (108) may be applied to the guidewire by any of a variety of methods, e.g., by spraying a solution or suspension of the polymers or of oligomers of the monomers onto the guidewire core or by dipping it into the solution or suspension. Initiators may be included in the solution or applied in a separate step. The guidewire may be sequentially or simultaneously dried to remove solvent after application of the polymer or oligomer to the guidewire and crosslinked.

The solution or suspension should be very dilute since only a very thin layer of polymer is to be applied. The amount of oligomer or polymer in such a solvent should be between 0.25% and 5.0% (wt), preferably is 0.5 to 2.0% (wt). Such a mixture is excellent for thin and complete coverage of the resulting polymer. Preferred solvents for this procedure when using the preferred polymers and procedure are water, low molecular weight alcohols, and ethers, especially methanol, propanol, isopropanol, ethanol, and their mixtures. Other water miscible solvents, e.g., tetrahydrofuran, methylene dichloride, methylethylketone, dimethylacetate, ethyl acetate, etc., are suitable for the listed polymers and must be chosen according to the characteristics of the polymer; they should be polar because of the hydrophilic nature of the polymers and oligomers but, because of the reactivity of the terminal groups of those materials, known quenching effects caused by oxygen, hydroxyl groups and the like must be recognized by the user of this process when choosing polymers and solvent systems.

Particularly preferred as an outer hydrophilic coating (108) for the guidewire core (104) discussed herein are physical mixtures of homo-oligomers of at least one of polyethylene oxide; poly 2-vinyl pyridine; polyvinylpyrrolidone, polyacrylic acid, polyacrylamide, and polyacrylonitrile. The catheter bodies or substrates are preferably sprayed or dipped, dried, and irradiated to produce a polymerized and crosslinked polymeric skin of the noted oligomers.

The lubricious hydrophilic coating (108) is preferably produced using generally simultaneous solvent removal and crosslinking operations. The coating is applied at a rate allowing "sheeting" of the solution, e.g., formation of a visibly smooth layer without "runs". In a dipping operation for use with most polymeric substrates including those noted below, the optimum coating rates are found at a linear removal rate between 0.25 and 2.0 inches/sec, preferably 0.5 and 1.0 inches/sec.

The solvent evaporation operations may be conducted using a heating chamber suitable for maintaining the surface at a temperature between 25° C. and the glass transition temperature ($T_g$) of the underlying tie layer or layers. Preferred temperatures are 50° C. to 125° C. Most preferred for the noted and preferred solvent systems is the range of 75° to 110° C.

Ultraviolet light sources may be used to crosslink the polymer precursors onto the substrate tie layer. Movement through an irradiation chamber having an ultraviolet light source at 90–375 nm (preferably 300–350 nm) having an irradiation density of 50–300 mW/cm$^2$ (preferably 150–250 mW/cm$^2$) for a period of three to seven seconds is desired. Passage of a guidewire core through the chamber at a rate of 0.25 to 2.0 inches/second (0.5 to 1.0 inches/second) in a chamber having three to nine inches length is suitable. When using ionizing radiation, a radiation density of 1 to 100 kRads/cm$^2$ (preferably 20 to 50 kRads/cm$^2$) may be applied to the solution or suspension on the polymeric substrate.

Exceptional durability of the resulting coating is produced by repetition of the dipping/solvent removal/irradiation steps up to five times. Preferred are two to four repetitions.

A tie layer (110) is shown in FIG. 1. A tie layer acts as a coating between the outer polymeric surface (108) and the guidewire core (104) to enhance the overall adhesion of that outer polymeric surface (108) to the core. Of course, the tie layer materials must be able to tolerate the various other solvents, cleaners, sterilization procedures, etc. to which the guidewire and its components are placed during other production steps.

Choice of materials for such tie layers is determined through their functionality. Specifically, the materials are chosen for their affinity or tenacity to the outer polymeric lubricious or hydrophilic coating. Clearly, the tie layer material must be flexible and strong. The material may be extrudable and perhaps formable into shrinkable tubing for mounting onto the guidewire through heating. The material may be placed onto the core wire using an exterior temporary heat shrink wrap tubing which is then removed. We have found that various polyamides (e.g., NYLON's), polyethylene, polystyrene, polyurethane, and polyesters, e.g., preferably polyethylene terephthalate (PET) make excellent tie layers. These tubing materials may be also formulated to include radio-opaque materials such as barium sulfate, bismuth trioxide, bismuth carbonate, tungsten, tantalum or the like.

As noted above, one readily achievable manner of applying a tie layer is by heat-shrinking the tubing onto the guidewire core (104). The guidewire core (104) is simply inserted into a tubing of suitable size—often with a small amount of a "caulking" at either end to seal the tubing from incursion of fluids or unsterile materials from beneath the tubing. The tubing is cut to length and heated until it is sufficiently small in size. The resulting tubing tie layer desirably is between about 0.25 and 1.5 mils in thickness. The thinner layers in the range are typically produced from polyurethane or PET. The layer of lubricious polymer (110) is then placed on the outer surface of the shrunk tubing.

Figure 2:
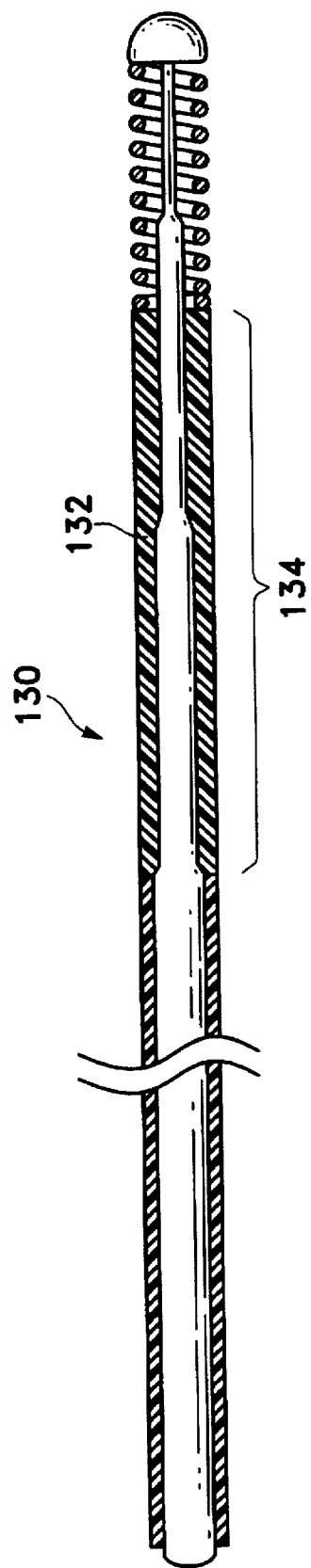

FIG. 2 shows another variation of the invention in which the catheter assembly (130) uses a single layer (132) of hydrophilic polymer on the exterior of the more distal region (134).

The procedure for preparing or pretreating the inventive guidewire (130) prior to receiving a subsequent coating of a lubricious, biocompatible, and hydrophilic polymer is via the use of a plasma stream to deposit a hydrocarbon or fluorocarbon residue. The procedure is as follows: the guidewire core is placed in a plasma chamber and cleaned with an oxygen plasma etch. The guidewire core is then exposed to a hydrocarbon plasma to deposit a plasma-polymerized tie layer on the guidewire core to complete the pretreatment. The hydrocarbon plasma may comprise a lower molecular weight (or gaseous) alkanes such as methane, ethane, propane, isobutane, butane or the like; lower molecular weight alkenes such as ethene, propene, isobutene, butene or the like or; gaseous fluorocarbons such as tetrafluoromethane, trichlorofluoromethane, dichlorodifluoromethane, trifluorochloromethane, tetrafluoroethylene, trichlorofluoroethylene, dichlorodifluoroethylene, trifluorochloroethylene and other such materials. Mixtures of these materials are also acceptable. The tie layer apparently provides C—C bonds for subsequent covalent bonding to the outer hydrophilic polymer coating. Preferred flow rates for the hydrocarbon into the plasma chamber are in the range of 500 c.c./min. to 2000 c.c./min. and the residence time of the guidewire in the chamber is in the range of 1–20 minutes, depending on the chosen hydrocarbon and the plasma chamber operating parameters. Power settings for the plasma chamber are preferably in the range of 200 W to 1500 W.

A tie layer of plasma-produced hydrocarbon residue having a thickness on the order of 10 Å thick is disposed between core and coating. This process typically produces layers of hydrocarbon residue less than about 1000 Å in thickness, and more typically less than about 100 Å. Tie layer effectively bonds the outer layer to the guidewire core while adding very little additional bulk to the guidewire.

The pretreated guidewire may then be coated by a hydrophilic polymer using a procedure such as described above. For example, the pretreated guidewire may be dipped in a solution of a photoactive hydrophilic polymer system, i.e., a latently photoreactive binder group covalently bonded to a hydrophilic polymer. After drying, the coated guidewire is cured by exposing it to UV light. The UV light activates the latently reactive group in the photoactive polymer system to form covalent bonds with crosslinked C—C bonds in the hydrocarbon residue tie layer. The dipping and curing steps are preferably repeated often enough, typically twice, to achieve the appropriate thickness of the hydrophilic coating layer.

The exterior surface of the guidewire is preferably a biocompatible coating of a polyacrylamide/polyvinylpyrrolidone mixture bonded to a photoactive binding agent. The preferred coating is made from a mixture of Bio-Metric Systems PA03 and PV05 (or PV01) binding systems according to the Examples below.

The photoactive hydrophilic polymer system of this preferred embodiment is a mixture of Bio-Metric Systems PA03 polyacrylamide/binder system and Bio-Metric Systems PV05 polyvinylpyrrolidone system. The polyacrylamide system provides lubricity; and the polyvinylpyrrolidone system provides both lubricity and binding for durability. The exact proportions of the two systems may be varied to suit the application. As an alternative, however, the hydrophilic biocompatible coating may be polyacrylamide alone, polyvinylpyrrolidone alone, polyethylene oxide, or any suitable coating known in the art.

In addition, a coating of heparin, albumin or other proteins may deposited over the hydrophilic coating in a manner known in the art to provide additional biocompatibility features both in the FIG. 1 and FIG. 2 variations.

The guidewire or other device may be cleaned by using an argon plasma etch in place of the oxygen plasma etch. The thickness of the plasma-polymerized tie layer may also vary without departing from the scope of this invention.

The following example is further illustrative of the articles and methods of this invention. The invention is not limited to these examples.

Although preferred embodiments of the present invention have been described, it should be understood that various changes, adaptations, and modifications may be made therein without departing from the spirit of the invention and the scope of the claims which follow.

I claim as my invention:

1. A guidewire suitable for guiding a catheter within a body lumen, comprising an elongated, flexible stainless steel alloy wire core having a more proximal section and a more distal section wherein the more proximal section is stiffer than the more distal section and has an outer proximal covering placed coaxially about and directly upon said wire core and said outer proximal covering is of a material selected from the group consisting of fluorocarbon polymers, polyarylenes, and polysulfones and wherein the more distal section has an outer distal covering axially adjacent said outer proximal covering and said outer distal covering comprising a tie layer adjacent the wire core, said tie layer being of a material selected from the group consisting of polyamides, polyethylene, polystyrene, polyurethane, and polyesters, said outer distal further comprising a hydrophilic polymeric composition exterior to said tie layer.

2. The guidewire of claim 1 wherein the more distal section and the more proximal section have the same outer diameter.

3. The guidewire of claim 1 wherein the tie layer is selected from polyethylene terephthalate and polyurethane.

4. The guidewire of claim 1 wherein the core wire is of a material selected from the group consisting of 303, 304, 304V, and 316 stainless steels.

5. The guidewire of claim 1 where the tie layer is a heat shrunk tubing.

6. The guidewire of claim 1 where the tie layer is a melted onto the core wire.

7. The guidewire of claim 1 where the tie layer further comprises a radiopaque material.

8. The guidewire of claim 1 where the tie layer is deposited by plasma.

9. The guidewire of claim 1 additionally comprising a catheter sheath.

\* \* \* \* \*